United States Patent
Xu et al.

(10) Patent No.: US 10,640,813 B2
(45) Date of Patent: May 5, 2020

(54) EXCHANGE-INDUCED REMNANT MAGNETIZATION FOR LABEL-FREE DETECTION OF DNA, MICRO-RNA, AND DNA/RNA-BINDING BIOMARKERS

(71) Applicant: University of Houston System, Houston, TX (US)

(72) Inventors: Shoujun Xu, Houston, TX (US); Li Yao, Houston, TX (US); Yuhong Wang, Houston, TX (US); Qiongzheng Hu, Houston, TX (US); Haopeng Yang, Houston, TX (US)

(73) Assignee: University of Houston System, Houston, TX (US)

( * ) Notice: Subject to any disclaimer, the term of this patent is extended or adjusted under 35 U.S.C. 154(b) by 0 days.

(21) Appl. No.: 16/170,208

(22) Filed: Oct. 25, 2018

(65) Prior Publication Data

US 2019/0048403 A1     Feb. 14, 2019

Related U.S. Application Data (63) Continuation of application No. 14/247,953, filed on Apr. 8, 2014, now abandoned.

(60) Provisional application No. 61/810,575, filed on Apr. 10, 2013.

(51) Int. Cl.
*C12Q 1/6825* (2018.01)

(52) U.S. Cl.
CPC .................. *C12Q 1/6825* (2013.01)

(58) Field of Classification Search
None
See application file for complete search history.

(56) References Cited

U.S. PATENT DOCUMENTS

| | | | |
|---|---|---|---|
| 2004/0009514 A1 | 1/2004 | Frutos | |
| 2010/0009456 A1* | 1/2010 | Prins | G01N 33/558 436/164 |
| 2010/0292094 A1* | 11/2010 | Lapointe | C12Q 1/6886 506/9 |

FOREIGN PATENT DOCUMENTS

WO     2011/080068     7/2011

OTHER PUBLICATIONS

Catuogno et al. Cancers 2011; 3: 1877-1898 (Year: 2011).*
International Search Report and Written Opinion for PCT/US2014/033370 dated Sep. 18, 2014 (11 pages).
Chinese Patent Application No. 201480030154.3 First Office Action dated Jun. 1, 2017 (17 pages).
Graham, et al., "Magetic field-assisted DNA hybridisation and simultaneous detection using micron-sized spin-valve sensors and magnetic nanoparticles," Sensors and Actuators B 107, 2005, pp. 936-944.

(Continued)

*Primary Examiner* — Angela M. Bertagna
(74) *Attorney, Agent, or Firm* — Conley Rose, P.C.

(57) ABSTRACT

A method of using an exchange-induced remnant magnetization (EXIRM) technique for label free detection of short strands of nucleotides and cancer biomarkers, such as DNA and microRNA strands, DNA/RNA-binding biomarkers, and cancer-specific antigens, with high sensitivity, high specificity, and broad dynamic range. The method may provide a label-free approach aimed to facilitate high reliability, and to require a minimum amount of biochemical reagents.

8 Claims, 5 Drawing Sheets

Specification includes a Sequence Listing.

Aligned magnetic particle      Random magnetic particle (56) References Cited

OTHER PUBLICATIONS

Obernosterer, et al., "Locked nucleic acid-based in situ detection of microRNAs in mouse tissue sections," Nature Protocols, vol. 2, No. 6, 2007, pp. 1508-1514.
Sudo, et al., "Use of Non-Amplified RNA Samples for Microarray Analysis of Gene Expression," PLoS ONE, vol. 7, Issue 2, 2012, e31397, pp. 1-6.
Fang, et al., "Attomole Microarray Detection of MicroRNAs by Nanoparticle-Amplified SPR Imaging Measurements of Surface Polyadenylation Reactions," Journal of American Chemical Society, 128, 2006, pp. 14044-14046.
Driskell, et al., "Rapid microRNA (miRNA) detection and classification via surface-enhanced Raman spectroscopy (SERS)," Biosensors and Bioelectronics, 24, 2008, pp. 917-922.
Yang, et al., "Direct, Electronic MicroRNA Detection for the Rapid Determination of Differential Expression Profiles," Angew. Chem. Int. Ed., 48, 2009, pp. 8461-8464.
Yao, et al., "Label-free microRNA detection based on exchange-induced remnant magnetization," The Royal Society of Chemistry, Chem. Commun., 49, 2013, pp. 5183-5185.
Yao, et al., "Long-Range, High-Resolution Magnetic Imaging of Nanoparticles," Ange. Chem. Int. Ed., 48, 2009, pp. 5679-5682.
European Patent Application No. 14729762.6 Examination Report dated Sep. 22, 2016 (9 pages).
European Patent Application No. 14729762.6 Examination Report dated Apr. 11, 2017 (7 pages).
European Patent Application No. 14729762.6 Examination Report dated Mar. 2, 2018 (5 pages).

\* cited by examiner

SEQUENCE LISTING

<160> NUMBER OF SEQ ID NOS: 9

<210> SEQ ID NO 1
<211> LENGTH: 22
<212> TYPE: DNA
<213> ORGANISM: Artificial
<220> FEATURE:
<223> OTHER INFORMATION: synthetic

<400> SEQUENCE: 1
uugauauguu ggaugaugga gu          22

<210> SEQ ID NO 2
<211> LENGTH: 22
<212> TYPE: DNA
<213> ORGANISM: Artificial
<220> FEATURE:
<223> OTHER INFORMATION: synthetic

<400> SEQUENCE: 2
aactatacaa cctactacct ca                                          22

<210> SEQ ID NO 3
<211> LENGTH: 22
<212> TYPE: DNA
<213> ORGANISM: Artificial
<220> FEATURE:
<223> OTHER INFORMATION: Synthetic

<400> SEQUENCE: 3
uuguuauguu ggaugaugga gu                                          22

<210> SEQ ID NO 4
<211> LENGTH: 22
<212> TYPE: DNA
<213> ORGANISM: Artificial
<220> FEATURE:
<223> OTHER INFORMATION: Synthetic

<400> SEQUENCE: 4
aaccatacaa cctactacct ca                                          22

<210> SEQ ID NO 5
<211> LENGTH: 22
<212> TYPE: DNA
<213> ORGANISM: Artificial
<220> FEATURE:
<223> OTHER INFORMATION: synthetic

<400> SEQUENCE: 5
uugguauguu ggaugaugga gu                                          22

<210> SEQ ID NO 6
<211> LENGTH: 22
<212> TYPE: DNA
<213> ORGANISM: Artificial
<220> FEATURE:
<223> OTHER INFORMATION: Synthetic

<400> SEQUENCE: 6
uugguauguu ggaugaugga gu                                          22

<210> SEQ ID NO 7
<211> LENGTH: 12
<212> TYPE: DNA
<213> ORGANISM: Artificial
<220> FEATURE:
<223> OTHER INFORMATION: Synthetic

<400> SEQUENCE: 7
cccaaaaatc cc                                                     12

<210> SEQ ID NO 8
<211> LENGTH: 12
<212> TYPE: DNA
<213> ORGANISM: Artificial
<220> FEATURE:
<223> OTHER INFORMATION: Synthetic

<400> SEQUENCE: 8
cccaaaaaac cc                                                     12

<210> SEQ ID NO 9
<211> LENGTH: 12
<212> TYPE: DNA
<213> ORGANISM: Artificial

```
<220> FEATURE:
<223> OTHER INFORMATION: Synthetic

<400> SEQUENCE: 9
gggaaaaaag gg                                                          12
```

EXCHANGE-INDUCED REMNANT MAGNETIZATION FOR LABEL-FREE DETECTION OF DNA, MICRO-RNA, AND DNA/RNA-BINDING BIOMARKERS

CROSS-REFERENCE TO RELATED APPLICATIONS

This application is a continuation of U.S. patent application Ser. No. 14/247,953, filed Apr. 8, 2014 (now abandoned), which claims priority to U.S. Provisional Patent Application No. 61/810,575, filed Apr. 10, 2013, the content of each being hereby incorporated by reference in their entirety for all purposes.

STATEMENT REGARDING FEDERALLY SPONSORED RESEARCH OR DEVELOPMENT

This invention was made with government support under grant no. ECCS-1028328 awarded by the National Science Foundation. The government has certain rights in the invention.

BACKGROUND

Field of the Invention

The present disclosure relates to the fields of miRNA profiling and biomarker detection.

Background

Nucleotides are biological molecules that form the building blocks of nucleic acids (DNA and RNA) and serve to carry packets of energy within the cell (ATP). In the form of the nucleoside triphosphates (ATP, GTP, CTP and UTP), nucleotides play central roles in metabolism. In addition, nucleotides participate in cell signaling (cGMP and cAMP), and are incorporated into important cofactors of enzymatic reactions (e.g. coenzyme A, FAD, FMN, NAD, and $NADP^+$). Nucleotides may also comprise synthetic sequences, and comprise chemical modifications to the nucleotide structure to produce for example nucleotide analogues.

DNA and RNA are biological molecules that are essential to life. Genetic information is encoded as specific sequences of DNA molecules. The information is passed along during transcription and protein synthesis via messenger RNA. Therefore, they are closely related, and interplay with various types of diseases, such as cancers.

In particular, miRNAs play a significant role in gene regulation, and are consequently a major category of biomarkers for cancer diagnostics. Because of their short strands and diverse expression levels, it remains technically challenging to achieve precise and quantitative detection. MiRNAs which are short RNA strands containing 18-25 nucleotides, play numerous important roles, including those in gene expression, development, and cell differentiation (1-3). The mature miRNAs incorporate into RNA-induced silencing complexes that bind with messenger RNAs based on partial sequence complementarity and consequently cause inhibition of protein translation. The regulation by miRNAs depends on their sequence, expression level, and cooperation with other miRNAs. Therefore, sensitive and specific detection of miRNAs is an essential step towards understanding their roles in protein synthesis, cell death, and as biomarkers of disease.

A range of techniques have been used for miRNA profiling. Known methods include northern blotting (4), reverse transcriptase polymerase chain reaction (5), in situ hybridization (6), microarray (7), bioluminescence (8), surface plasmon resonance (9), surface-enhanced Raman spectroscopy (10), electrochemical detection (11), fluorescence (12), and photonic methods (13); however, no single technique achieves high sensitivity, single-base specificity, and broad dynamic range. In addition, reproducibility remains a significant issue when comparing results from different techniques, due to the many steps and various protocols involved in analysis (14). Hence there is an unmet need in the field for a single technique that can detect short nucleotide sequences such as miRNA, with high sensitivity, high specificity, and broad dynamic range, which may be a one-step method that facilitates high reliability, and needs minimum amount of biochemical reagents.

Thus, the production of a method capable of accurately detecting short nucleotide sequences, (DNA or RNA sequences such as miRNA) with high sensitivity, high specificity, and broad dynamic range would be particularly well received, and embodiments of the herein presented method are believed to overcome certain above mentioned limitations by the utilization an exchange-induced remnant magnetization (EXIRM) technique (15).

In addition, many cancer biomarkers can specifically bind with short DNA strands, for example prostate specific antigen (16). The EXIRM method can be directly modified to achieve sensitive and label-free detection of such cancer biomarkers.

BRIEF SUMMARY OF THE DISCLOSED EMBODIMENTS

The present disclosure relates to a method of using an exchange-induced remnant magnetization (EXIRM) technique for detecting short strands of nucleotides, such as those comprising deoxyribonucleic acid (DNA); and those comprising ribonucleic acid (RNA), including microRNA (miRNA), with high sensitivity, high specificity, and broad dynamic range. Further, the method herein described may also be a one-step method that facilitates high reliability, and requires a minimum amount of biochemical reagents.

Certain embodiments herein described address such needs, and uses sequence-specific exchange reactions between label-free nucleotide sequences (for example miRNA) and magnetically labelled nucleotide sequences (for example RNA, miRNA, or DNA) with, in some embodiments a one base difference. In one embodiment, the exchange-induced remnant magnetization (EXIRM) quantitatively measures a target miRNA with single-base specificity, and in some embodiments the detection limit of such target miRNAs reach zeptomolar levels. In a further embodiment, two miRNAs with only one base difference may be detected in parallel while showing no magnetic signal crosstalking, and in still further embodiments, the EXIRM technique analyses miRNA without any amplification or washing procedures. In some embodiments the EXIRM method herein described is suitable for precise miRNA profiling for early diagnosis and precise prognosis of cancers. The method can also be extended, wherein some embodiments a sample of interest for which a quantitative measurement is required may comprise a protein or a derivative thereof, and in a further embodiment a sample may comprise an antibody. Further such measurements may also be performed directly in a biological environment such as but not limited to blood plasma, urine, or cell lysate, and or other environments with limited optical detection.

In one embodiment, a method of detecting nucleotide sequences comprises: (a) immobilizing a first nucleotide single strand on a surface; (b) adding a second nucleotide single strand to the first nucleotide single strand to form a hybridized double strand, where the second strand comprises a first magnetic particle; and a nucleotide sequence that is less than 100% complementary to the first nucleotide single strand, and comprises at least a first mismatched base; (c) measuring a first magnetic signal value for the hybridized double strand; (d) incubating a third nucleotide strand with the hybridized double strand; wherein the third strand is complementary to the first strand, and wherein incubating forms an exchange product; (e) measuring a second magnetic signal value for the exchange product of step d; and (f) quantifying the amount of the third nucleotide strand from the difference in magnetic signal values measured in step c and step e.

In some embodiments of the method of detecting nucleotide sequences, the first nucleotide single strand is derivatized; in some other embodiments the first nucleotide strand may be biotinylated or thiol captured. In another embodiment of the method of detecting nucleotide sequences the first nucleotide strand is immobilized to a surface through a S—Au covalent bond. In a further embodiment of the method of detecting nucleotide sequences, a magnetic particle is attached to the second nucleotide strand by a streptavidin-biotin covalent bond. In another embodiment the magnetic particle is about 1 nm to about 10 μm in size (for example, diameter of spherical magnetic particles). in a further embodiment about 10 nm to about 5 μm in size, and in a further embodiment the magnetic particle is about 3 μm in size.

In another embodiment of the method of detecting nucleotide sequences, measuring comprises an atomic magnetometer; in a further embodiment, the first and the second magnetic signal values comprise magnetic moment measurements (17), and in another embodiment of the method of detecting nucleotide sequences, step (f) comprises measuring the change in magnetic signal ($\Delta B$), and in some further embodiments the molar concentration of the third nucleotide strand may be calculated wherein the molar concentration is linearly related to $\Delta B$ or the change in magnetic moment measurements. In some embodiments of the method of detecting nucleotide sequences, quantifying further comprises calculating the number of free magnetic particle labels, wherein the number of said free magnetic particles corresponds to the number of exchange product molecules.

In some embodiments of the method of detecting nucleotide sequences, the surface is in a sample holder. In one embodiment, the hybridized double stranded sequence is in a liquid environment. In further embodiment the environment is a cell lysate, and in a still further embodiment the environment is blood plasma, and in a further embodiment, the environment is urine.

In some embodiments of the method of detecting nucleotide sequences, the first nucleotide strand is a RNA or a DNA sequence, in another embodiment the third nucleotide strand is a DNA or microRNA sequence. In some embodiments, the first nucleotide strand is about 1-100 nucleotides in length, in some further embodiments, the second nucleotide strand is about 1-100 nucleotides in length, and in some still further embodiments the third nucleotide strand is about 1-100 nucleotides in length.

In some embodiments, the first nucleotide strand is about 10-50 nucleotides in length, in some further embodiments, the second nucleotide strand is about 10-50 nucleotides in length, and in some still further embodiments the third nucleotide strand is about 10-50 nucleotides in length.

In some embodiments, the first nucleotide strand is about 18-25 nucleotides in length, in some further embodiments, the second nucleotide strand is about 18-25 nucleotides in length, and in some still further embodiments the third nucleotide strand is about 18-25 nucleotides in length.

In some embodiments, the first nucleotide strand is about 18-25 nucleotides in length, in some further embodiments, the second nucleotide strand is replaced by the DNA/RNA-binding biomarker, and in some still further embodiments the third nucleotide strand is about 18-25 nucleotides in length.

In other embodiments of the method of detecting nucleotide sequences, the exchange product is thermodynamically more stable than the hybridized double strand, in some embodiments the double strand is 12 pN (pN: $10^{-12}$N) less stable than said exchange product.

In another embodiment, a method of simultaneously detecting an array of heterologous nucleotide sequences is provided wherein the method comprises: (a) coating a sample well comprising an array of compartment; wherein the surface of adjacent compartments are alternatively coated with i) a hybridized nucleotide double strand; and ii) are uncoated; wherein the uncoated compartment produces no magnetic signal; and each coated compartment comprises a heterologous hybridized double strand sequence; (b) measuring magnetic signals for each compartment; (c) incubating the array with a sample comprising free target nucleotide sequences, and forming exchange products; (d) measuring magnetic signals for each compartment comprising exchange products after applying a weak mechanical force to remove nonspecifically bound magnetic particles; (e) calculating the difference in said signals from step b and d; and (f) quantifying and identifying said target sequence based on the change in signal calculated in step (e). In a further embodiment of the method of simultaneously detecting an array of heterologous nucleotide sequences measuring the magnetic signal from the sample array is by: a scanning single sensor, scanning the sample well, a two-dimensional sensor array for simultaneous detection or combinations thereof.

In another embodiment, an exchange induced remnant magnetization method to detect specific nucleotide sequences is herein described, the method comprising: (a) immobilizing a first single stranded sequence on a surface; wherein the first sequence comprises N bases; (b) adding a second single stranded sequence to the first single stranded sequence, wherein the second single stranded sequence comprises N−1 complementary bases; wherein said complementary bases are complementary to the sequence of the first single strand sequence, and wherein the second single stranded sequence hybridizes to the first single stranded sequence forming a hybridized double stranded sequence with N−1 base pairs; and (c) incubating the hybridized double stranded sequence with a third single stranded sequence, wherein the third single stranded sequence comprises N complementary bases, wherein said complementary bases are complementary to the sequence of the first single strand sequence; and wherein said third single stranded sequence exchanges with said second single stranded sequence to form an exchange product comprising a double strand with N complementary base pairs; wherein said exchange product is thermodynamically more stable than said hybridized double stranded sequence. Further embodiments may include species wherein the second single stranded sequence is mismatched by greater that one complementary base.

In another embodiment, an exchange induced remnant magnetization method to detect specific biomarkers is herein described, the method comprising: (a) immobilizing a first single stranded sequence on a surface; wherein the first sequence comprises N bases; (b) adding a second single stranded sequence to the first single stranded sequence, wherein the second single stranded sequence comprises N complementary bases; wherein said complementary bases are complementary to the sequence of the first single strand sequence, and wherein the second single stranded sequence hybridizes to the first single stranded sequence forming a hybridized double stranded sequence with N base pairs; and (c) incubating the hybridized double stranded sequence with a biomarker, wherein the biomarker exchanges with said second single stranded sequence to form an exchange product comprising a DNA-biomarker complex; wherein said exchange product is thermodynamically more stable than said hybridized double stranded sequence. Further embodiments may include species wherein the second single stranded sequence is mismatched by one complementary base or more.

Thus, embodiments described herein comprise a combination of features and characteristics intended to address various shortcomings associated with certain methods of detecting nucleotide sequences such as DNA and microRNA sequences, wherein the exchange-induced remnant magnetization technique described detects such sequences with high sensitivity, high specificity, and over a broad dynamic range as compared to some techniques known in the art. The various features and characteristics described above, as well as others, will be readily apparent to those skilled in the art upon reading the following detailed description, and by referring to the accompanying drawings.

BRIEF DESCRIPTION OF THE DRAWINGS

For a detailed description of the disclosed embodiments, reference will now be made to the accompanying drawings, wherein:

FIG. 8 (A-E) depicts EXIRM for multiplexed miRNA analysis with single-base specificity; (A) shows the MiRNA sequences let-7a (Seq. ID NO. 1, of the sequence listing as filed), 1a (Seq. ID NO. 2, of the sequence listing as filed); 2 (Seq. ID NO. 3, of the sequence listing as filed); 1b (Seq. ID NO. 4, of the sequence listing as filed); let-7c ((Seq. ID NO. 5, of the sequence listing as filed) respectively; which are used in the corresponding experiment; and bases that are used for the analysis are in red (fourth line) with the mismatching bases underlined; (B) shows an image depicting a sample holder with two sample wells; (C); (D); and (E) depict the magnetic signal change for adding let-7c (C), let-7a (D), and no miRNA (E) into both of the sample wells shown in B; The dashed lines in C,D, and E, show the positions of the two sample wells.

DETAILED DESCRIPTION OF DISCLOSED EMBODIMENTS

Embodiments herein addressed are intended to overcome certain above mentioned limitations by using a method for an exchange-induced remnant magnetization (EXIRM) technique for detecting DNA, microRNA, and DNA/RNA-binding proteins with high sensitivity, high specificity, and broad dynamic range (15). Herein and throughout the application, the term "strand" and "sequence" may be used interchangeably to describe sequences of nucleotides which are single stranded. Similarly, "hybridized strand," "hybridized double strand," "hybridized double stranded sequence" or "hybridized sequence" may be used interchangeably. As used herein, the term "about," when used in conjunction with a percentage or other numerical amount, means plus or minus 10% of that percentage or other numerical amount. For example, the term "about 80%," would encompass 80% plus or minus 8%. Further, all references cited herein are incorporated in their entirety.

General Principle

In some embodiments, an exchange induced remnant magnetization method to detect specific nucleotide sequences is herein described, the method comprises: (a)

immobilizing a first single stranded sequence on a surface; wherein the first sequence comprises N bases; (b) adding a second single stranded sequence to the first single stranded sequence, wherein the second single stranded sequence comprises N−1 complementary bases; wherein said complementary bases are complementary to the sequence of the first single strand sequence, and wherein the second single stranded sequence hybridizes to the first single stranded sequence forming a hybridized double stranded sequence with N−1 base pairs; and (c) incubating the hybridized double stranded sequence with a third single stranded sequence, wherein the third single stranded sequence comprises N complementary bases; and wherein said third single stranded sequence exchanges with said second single stranded sequence to form an exchange product comprising a double strand with N complementary base pairs; wherein said exchange product is thermodynamically more stable than said hybridized double stranded sequence.

In some embodiments, a method of detecting nucleotide sequences is herein described, comprising (a) immobilizing a first nucleotide single strand on a surface; (b) adding a second nucleotide single strand to the first nucleotide single strand to form a hybridized double strand, where the second strand comprises a first magnetic particle; and a nucleotide sequence that is less than 100% complementary to the first nucleotide single stand, and comprises at least a first mismatched base; (c) measuring a first magnetic signal value for the hybridized double strand; (d) incubating a third nucleotide strand with the hybridized double strand; wherein the third strand is complementary to the first strand, and wherein incubating forms an exchange product; (e) measuring a second magnetic signal value for the exchange product of step d after applying a weak mechanical force to remove nonspecifically bound magnetic particles; and (f) quantifying the amount of the third nucleotide strand from the difference in magnetization value measured in step c and step e.

Figure 1:
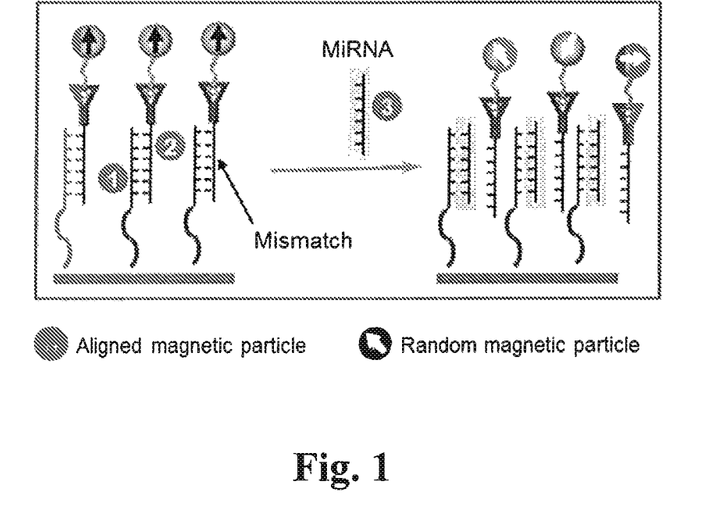
FIG. 1 depicts an embodiment of the EXIRM technique described herein, where three RNA strands are involved: immobilized Strand 1, hybridized Strand 2 with one mismatching base, and Strand 3 which is the target miRNA. Strand 2 is labelled by magnetic particles (the approach may also be applied to DNA)

Thus, in one embodiment of the invention herein described, a specific nucleotide sequence such as (but not limited to) a miRNA sequence can be detected by magnetic signal changes caused by exchange reactions between a target miRNA sequence and a magnetically labelled RNA sequence with a single nucleotide base difference; as illustrated in the embodiment of FIG. 1, a hybridized RNA double strand is first prepared, a strand composed of nucleotide bases that compliments the target miRNA (Strand 1) is immobilized on the surface of a sample well/plate, and a second strand (Strand 2) composed of nucleotide bases that differ (are mismatched) by (at least) one base from Strand 1, and the target miRNA (Strand 3) is further labelled with a magnetic particle. Strand 1 and Strand 2 form a hybridized double strand of RNA, immobilized on the surface through Strand 1 and magnetically labelled through Strand 2.

The target miRNA is then incubated with the hybridized double strand in the sample well. An exchange reaction then takes place, in which the target miRNA replaces the mismatching strand because the former has thermodynamically stronger binding with the immobilized RNA than the latter. When the strands with one mismatching base (hybridized pair) which are immobilized and magnetically labelled undergo magnetization by a strong magnet (>0.1 Tesla), the magnetic dipoles of the particles are aligned and produce a strong magnetic signal; hence when the mismatching RNA undergoes dissociation from the immobilized strand due to the thermodynamically favored binding of the complementary target strand, randomization of the magnetic dipoles of the magnetic labels occurs due to Brownian motion of the now free magnetically labelled strands which is induced by a weak mechanical force provided by a shaker or a centrifuge, or a sonicator. The exchange reaction thus produces a decrease in the magnetic signal ($\Delta B$ in pT), because of the randomization of the magnetic particles, which is measured by an atomic magnetometer (17), the decreasing amplitude of the signal thus represents the quantity of the target miRNA molecules Thus, in some embodiments of the method of detecting nucleotide sequences, the first nucleotide strand is a RNA or a DNA sequence, in another embodiment the third nucleotide strand is a DNA or microRNA sequence. In some embodiments, the first nucleotide strand is about 1-100 nucleotides in length, in some further embodiments, the second nucleotide strand is about 1-100 nucleotides in length, and in some still further embodiments the third nucleotide strand is about 1-100 nucleotides in length.

In some embodiments, the first nucleotide strand is about 10-50 nucleotides in length, in some further embodiments, the second nucleotide strand is about 10-50 nucleotides in length, and in some still further embodiments the third nucleotide strand is about 10-50 nucleotides in length. In some embodiments, the first nucleotide strand is about 18-25 nucleotides in length, in some further embodiments, the second nucleotide strand is about 18-25 nucleotides in length, and in some still further embodiments the third nucleotide strand is about 18-25 nucleotides in length. In some embodiments the second nucleotide single strand comprises 1-100 mismatched bases, in another embodiment the second nucleotide single strand comprises 1-50 mismatched bases, in another embodiment the second nucleotide single strand comprises 1-10 mismatched bases; and in a preferred embodiment the second nucleotide single strand comprises 1 mismatched based, wherein the definition of mismatched is that the base bonds with a second molecule or base that is not it's natural Watson and Crick base pair interaction i.e. guanine/cytosine bonding, adenine/thymine bonding and adenine/uracil bonding.

In other embodiments of the method of detecting nucleotide sequences, the exchange product is thermodynamically more stable than said hybridized double strand, in some embodiments the double strand is at least 12 pN less stable than said exchange product, wherein the stability declines based on the loss of hydrogen bonding between base pairs.

In some embodiments of the method of detecting cancer biomarkers, the exchange product of the DNA-biomarker complex is thermodynamically more stable than said hybridized double strand.

In some embodiments of the method of detecting nucleotide sequences, the first nucleotide single strand is derivatized; in some other embodiments the first nucleotide strand may be biotinylated or thiol captured. In another embodiment of the method of detecting nucleotide sequences, the first nucleotide strand is immobilized to a surface through a S—Au covalent bond. In a further embodiment of the method of detecting nucleotide sequences, a magnetic particle is attached to the second nucleotide strand by a streptavidin-biotin covalent bond. In another embodiment the magnetic particle is about 1 nm to about 10 μm in size, about 10 nm to about 5 μm in size, and in a further embodiment the magnetic particle is about 3 μm in size.

Detection Level and Sensitivity of the Method

Figure 2:
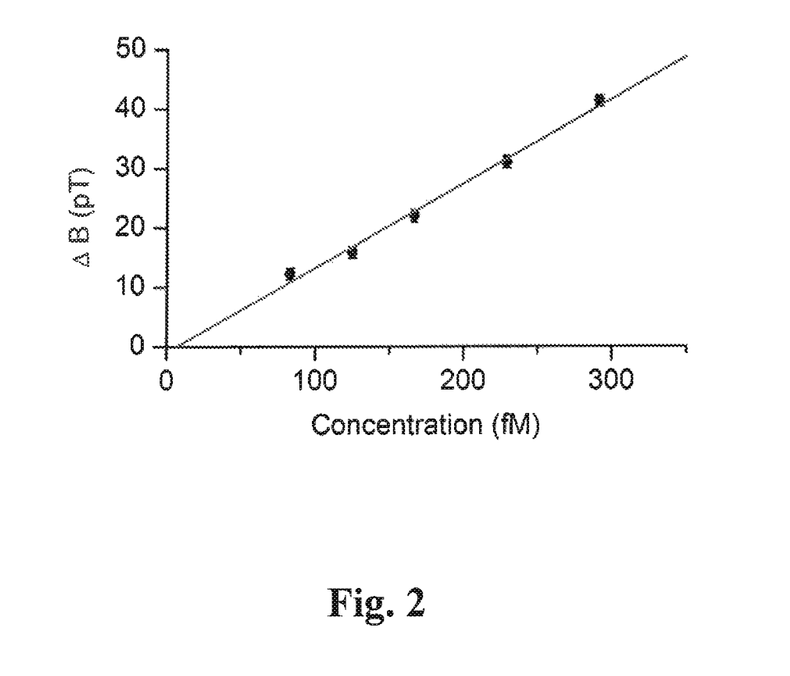
FIG. 2 depicts a plot of a magnetic signal changes ($\Delta B$ (in pT; $10^{-12}$ T)) for various concentrations (femto molar, $10^{-15}$ M) of the target DNA, wherein the linear correlation shows good quantification of the DNA molecules in accordance with principles described herein. The diameter of the magnetic particles is 2.8 µm in accordance with principles described herein.

The level of detection for the embodiments of the method herein described is obtained by varying the concentration of the target nucleotide sequences, for example the magnetic signal decrease ($\Delta B$) is plotted against the concentration of target nucleotides, in one such embodiment illustrated in FIG. 2, five different concentrations of a DNA target sequence were used, and EXIRM performed. The five measurements of ΔB were linearly correlated, and the linear fit goes through the origin, which indicates the high sensitivity of the method for measuring changes in magnetic signal at these concentrations, and that the quantification is highly reliable.

Figure 3:
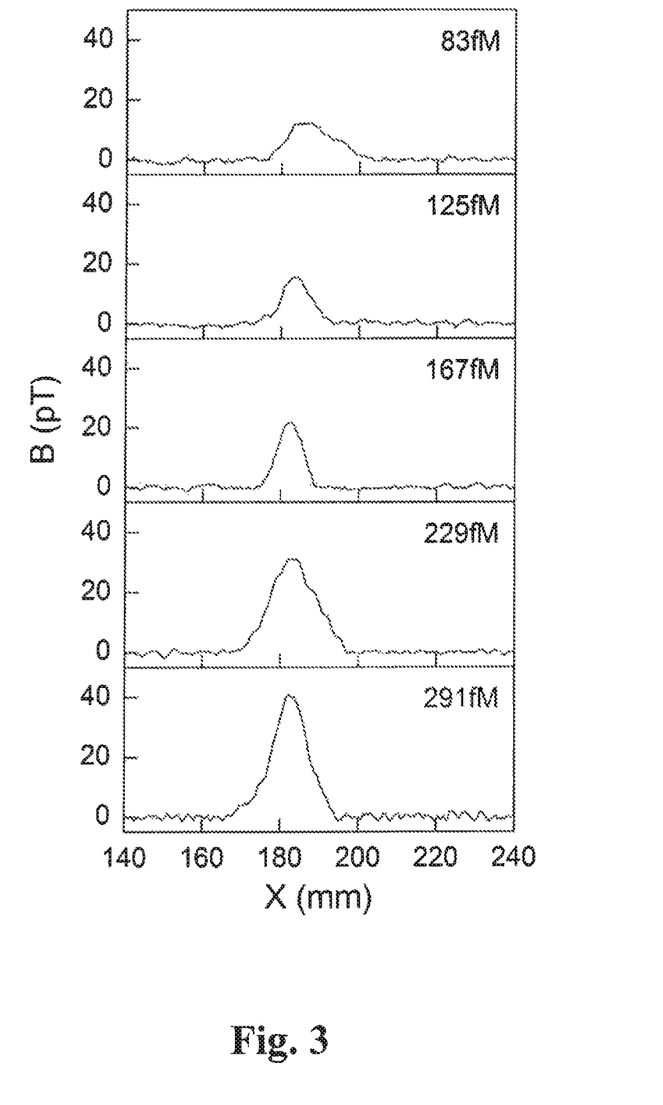
FIG. 3 depicts a graphic representation of normalized measurements with 1 second signal averaging for the 12-base DNA exchange reaction at five different concentrations; wherein the normalized profiles were obtained in this embodiment by averaging 33 adjacent data points in the raw data, where each data point was measured for 30 ms, the X-axis represents the relative position of the sample to the atomic sensor during scanning the sample, and performed in accordance with principles described herein.

In some embodiments, given a sample well with a known volume of 8 μL, the total number of the DNA sequences being replaced can be calculated to be 660 zeptomole, or $4 \times 10^5$ molecules, for the concentration of 83 fM. The error bars were obtained by normalizing the measuring time to 1 second, which was nearly 1 pT (FIG. 3). From the ΔB value of 12 pT for the 83 fM sample, the detection limit has already reached $3.3 \times 10^4$ molecules. Therefore, the detection limit is substantially better than other current techniques for DNA/RNA oligomers (18). In a further embodiment, based on the sensitivity of 150 fT of the apparatus (19), the detection level of the method can allow measurements of $6 \times 10^3$ molecules with 1 second signal averaging time.

Dynamic Range

The dynamic range of EXIRM is defined as the span between the number of target molecules that give the lowest detectable magnetic signal and the number of target molecules that give the highest detectable magnetic signal.

Figure 4:
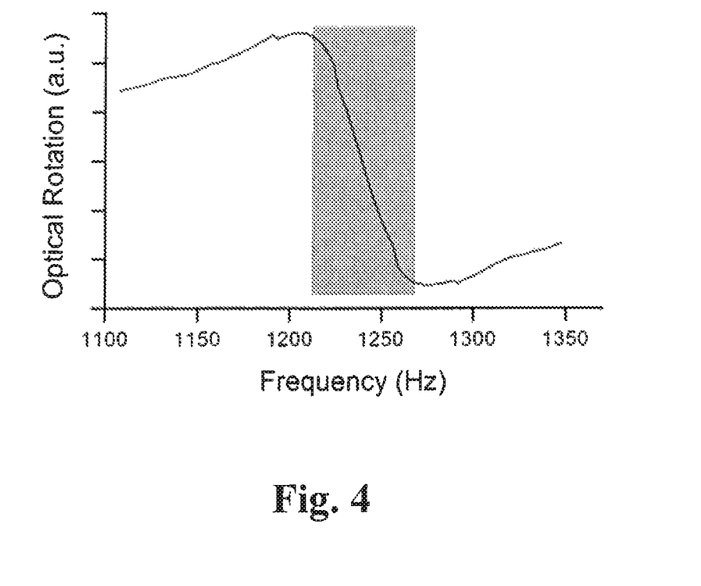
FIG. 4 depicts a plot of magneto-optical resonance to show the maximum measurable magnetic fields by the atomic magnetometer, wherein the highlighted rectangular area shows the responsive range of the atomic magnetometer to the samples magnetic signal, in accordance with principles described herein.

The dynamic range of embodiments of the method described herein, can be derived from the sensitivity of the magnetometer and the width of magneto-optical resonance. The latter represents the optical response by the magnetometer to the magnetic field to be measured. Therefore, it provides the range for the magnetic signal that the magnetometer is sensitive to. In some embodiments, a sensitivity of about 150 fT defines the lower end of the dynamic range. In some embodiments, given a resonance width of ~70 Hz for the magnetometer (FIG. 4, highlighted area) a frequency range (the horizontal axis) is the frequency change is almost linear to the magnetic signal. This width gives an upper measurement limit of about 10 nT, because $B=\omega/2\gamma$, where ω is the modulation frequency of the laser and γ of 3.5 Hz/nT is the gyromagnetic ratio for Cs (cesium, the atom for the atomic magnetometer shown here). Hence in one such embodiment, the dynamic range is about 5 orders of magnitude for a selected magnetic particle.

In another embodiment, a broad dynamic range is preferred for miRNA profiling, because it is well known that the expression levels may be drastically different for different miRNAs. Therefore in some embodiment's large numbers of miRNA are available for exchange wherein the signal change will be greater, while in other embodiments the number of miRNA expressed and available for exchange will be small. In one embodiment of the method herein described, the atomic magnetometer has an upper detection limit of approximately 10 nT; and the lower limit is determined by the sensitivity, which is 150 fT. Therefore, with a selected type of magnetic particles for labelling, the dynamic range is about five orders of magnitude as described above.

Figure 5:
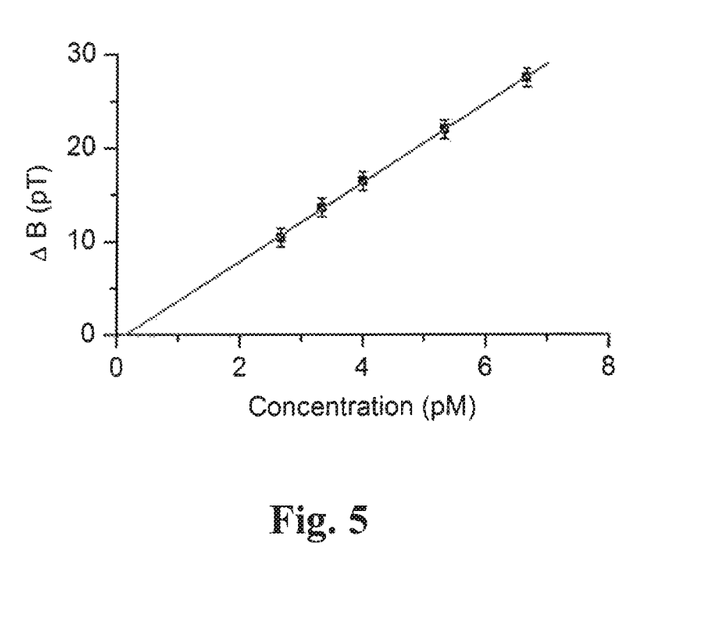
FIG. 5 depicts a plot of a magnetic signal changes $\Delta B$ (pT) for various concentrations of the target DNA using smaller magnetic particles, with diameter of 1 µm, and shows the quantitative relationship between the change in B with concentration of magnetic particle labelled DNA.

Furthermore, in some embodiments, the dynamic range in terms of number of miRNA molecules can be adjusted by tuning the magnetic property of the particles. This is because for magnetically weaker particles, a larger number of particles will be needed to reach the upper limit of the detection range. Hence more target molecules can be detected. While for magnetically stronger particles, a fewer number of particles will provide sufficient magnetic signal so that a fewer number of target molecules will be detected. Potentially single-molecule detection is achievable when the magnetic particle gives sufficiently strong signal (20). Therefore, again in some embodiments the dynamic range of EXIRM may be greater than five orders of magnitude. An example of using different sized magnetic particles to adjust the dynamic range is shown in FIG. 5.

Multiplexed Detection

In another embodiment, a method of simultaneously detecting an array of heterologous nucleotide sequences is provided wherein the method comprises: (a) coating a sample well comprising an array of squares; wherein the surface of adjacent squares are alternatively coated with i) a hybridized nucleotide double strand; and ii) remain uncoated; wherein the uncoated square produces no magnetic signal; and each coated square comprises a heterologous hybridized double strand sequence; (b) measuring magnetic signals for each square; (c) incubating the array with a sample comprising free target nucleotide sequences, and forming exchange products; (d) measuring magnetic signals for each square comprising exchange products; (e) calculating the difference in said signals from step b and d; and (f) quantifying and identifying said target sequence based on the change in signal calculated in step (e). In a further embodiment of the method of simultaneously detecting an array of heterologous nucleotide sequences measuring the magnetic signal from the sample array is by: a scanning single sensor, scanning the sample well, a two-dimensional sensor array for simultaneous detection or combinations thereof.

Thus, multiplexed detection is a simultaneous measurement or a method of identifying multiple species in a single experimental run. In some embodiments, multiplexed detection assays are experiments that endeavour to detect or to assay the state of all biomolecules of a given class (e.g., miRNAs) within a biological sample, to determine the effect of an experimental treatment or the effect of a DNA mutation over all of the biomolecules or pathways in the sample.

Figure 6:
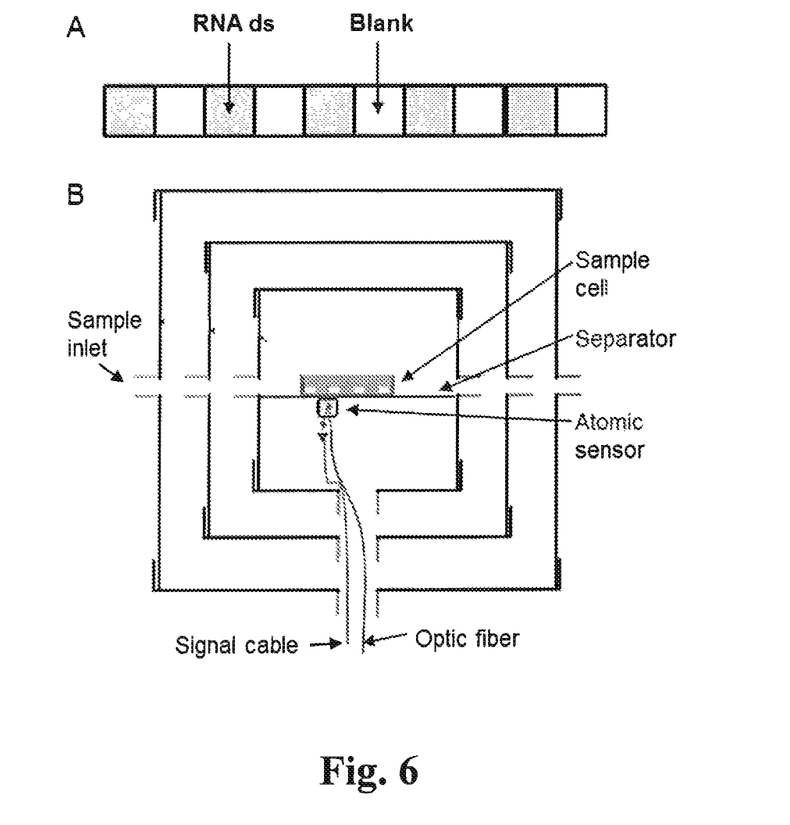
FIG. 6 depicts an illustration of multiplexed detection, in accordance with principles described herein and wherein (A) is a Schematic of an array of sample wells. Each golden square is for a specific target of RNA or DNA. Each blank separates two adjacent sample wells; and (B) is an example of detecting multiple targeted RNA or DNA. The atomic magnetometer is composed of an atomic sensor housed in a multi-layered magnetic shield, the sample cell containing an array of sample wells is introduced through a sample inlet channel through the magnetic shield, and an optical fiber may be used to deliver the laser beam to the atomic sensor. The signal comes out through a signal cable.

In some embodiments of the method herein described, multiplexed detection of arrayed samples is needed because miRNAs often do not function alone. It has been reported that groups of miRNAs play important roles cooperatively (21). In addition, miRNA expression is highly heterogeneous (22). Therefore, monitoring a group of miRNAs that may be closely related in sequence in a single sample is required. FIG. 6 shows an embodiment of a one-dimensional multiplexed detection. The bottom of a single sample well is patterned into an array of squares, which are alternatively coated with RNA double strands which have sequences that vary cell to cell, and a blank. Each coated square aims at targeting one type of miRNA sequence. In some embodiments, a blank square is needed in between two coated squares to avoid signal cross-talking that arises from the overlap of the magnetic signals. In one embodiment, 2 mm atomic sensors are used, thus each sample square is 2×2 mm², the distance between two adjacent samples is 4 mm center to center, and the area of the sample being 4×1 mm², thus in one such embodiment, a sample well with 2.6×2.6 cm² bottom area can analyze 49 different types of miRNAs. Smaller atomic sensors may be used for multiplexed detection of a greater number of different miRNAs if needed.

As such there are two ways to detect the magnetic signals from the sample array: one embodiment comprises a scanning single sensor, and another embodiment comprises using a two-dimensional sensor array for simultaneous detection. FIG. 6B shows a schematic of using the single sensor approach. The approach of using an array of sensors can be carried out similarly.

In some embodiments, no amplification is needed, and no washing or sample transfer is used. This simplifies the analysis procedure and improves the reliability of the measurements as compared to known techniques which often involve multiple steps of sample preparation, amplification, and multiple washing steps.

In some embodiments, the EXIRM technique described herein, provides a new avenue for miRNA analysis. In some embodiments, the high sensitivity of atomic magnetometers allows detection of about $10^4$ molecules; in further embodiments detection may be in the order of $10^3$ molecules. In other embodiments single-base specificity is achieved from the sequence-specific exchange reactions; and in further embodiments, cross-talking is not observed between miRNAs wherein in some embodiments, there is only a one base difference between sequences.

EXAMPLES

Example 1(A) EXIRM's Single-Base Specificity in DNA Detection

In one embodiment, to demonstrate EXIRM, three 12-base DNA strands were chosen. The nucleotide strand was a thiolated GGG AAA AAA GGG (Strand 1; SEQ ID NO: 9), which was loaded onto a sample well (of 4×2×1 mm3 in size) and subsequently immobilized on the bottom surface of the well via S—Au covalent bonds (15).

Figure 7:
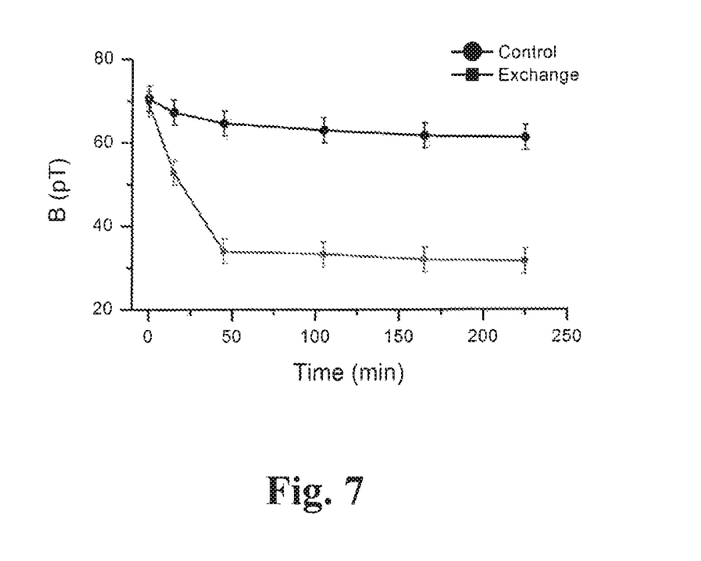
FIG. 7 depicts a plot of a magnetic signal as a function of reaction time for an EXIRM experiment; wherein a 12-base DNA was the target strand, which replaced another DNA with one-base difference that was pre-hybridized with the complementary strand to the former (in control, the target DNA was absent) performed in accordance with principles described herein.

The second strand was then added for hybridization, using biotinylated oligonucleotide sequences, CCC AAA AAT CCC (Strand 2; 11 base pair match to strand 1 (Seq. ID NO. 7, of the sequence listing as filed)) and was labelled with magnetic particles (examples of such magnetic particles include Streptavidin-coated 2.8 μm sized magnetic particles (Invitrogen, M280)). The target strand (CCC AAA AAA CCC (Strand 3 (Seq. ID NO. 8, of the sequence listing as filed))) which was fully complimentary to the immobilized strand (12 base pair match), was thus added to the sample well. This system was chosen because the force of Strand 1 binding to Strand 2 (11-base pair match) is 12 pN weaker than that of Strand 1 binding to Strand 3 (12 base pair match). The magnetic signal showed a decrease when Strand 3 was added into the sample well containing Strand 1-Strand 2 double helix (lower trace in FIG. 7). The decrease signal indicated the occurrence of the exchange reaction, in which Strand 3 replaced Strand 2. In contrast, when the target Strand 3 was absent, no magnetic signal decrease was observed (upper trace in FIG. 7). The magnetic signal profile also showed that the exchange reaction took less than one hour to complete at 37° C.

Example 1(B) EXIRM's Single-Base Specificity in Multiplexed MiRNA Analysis

Figure 8:
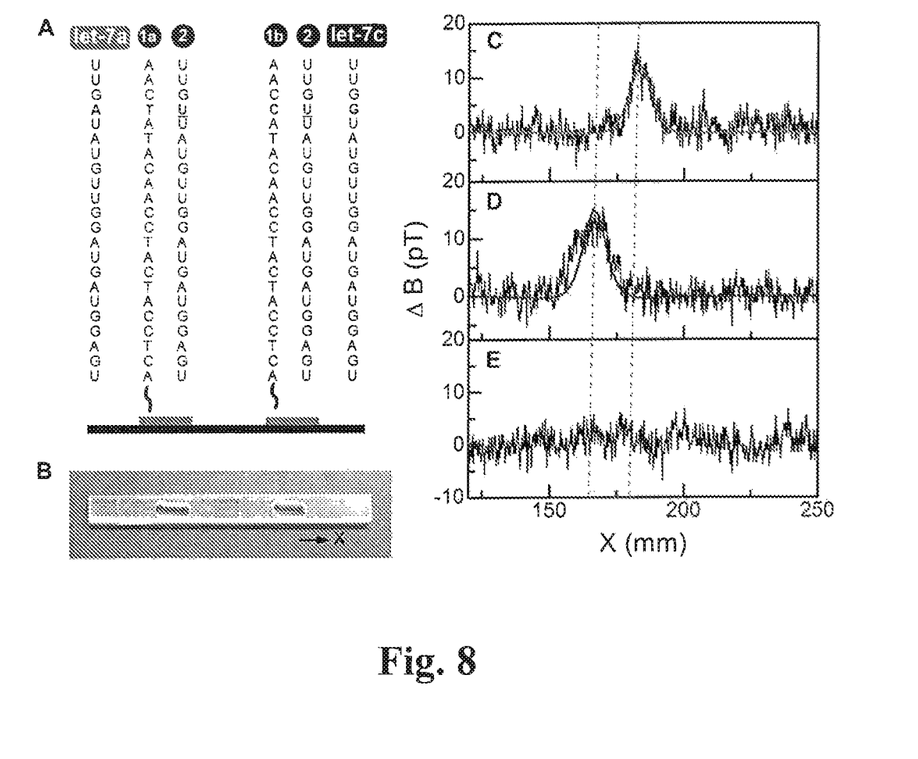

In one embodiment of the method herein described, two sample wells were placed in parallel along the sample holder (FIG. 8B), the two selected target miRNAs were let-7a and let-7c, which are biomarkers for lung cancer (21) and colorectal cancer (22) respectively, and the two miRNA only differ by one base as can be seen in FIG. 8A which shows the experimental sequences. In this embodiment, nucleotide Strand 1a is entirely complimentary (base by base) with let-7a and nucleotide Strand 1b is entirely complimentary (base by base match) with let-7c. The two sample wells used a common Strand 2, which had one mismatching base for both Strand 1a and Strand 1b. When let-7c was added to both sample wells, only the right sample well (located at 182 mm) gave a magnetic signal decrease, as depicted by the magnetic signal change ($\Delta B(pT)$) seen in FIG. 8C). This is because let-7c compliments Strand 1b and therefore replaces Strand 2 only in the right sample well. Let-7c is one-base mismatched for Strand 1a, thus no exchange reaction occurred in the left sample well (at 168 mm). Similarly, when let-7a was added to both sample wells, only the left sample well produced a magnetic signal decrease as depicted by the magnetic signal change ($\Delta B(pT)$) seen in FIG. 8D). As a control experiment, when no miRNA was added to the sample wells, no magnetic signal change was observed in either sample well as depicted in FIG. 8E. This confirms the responses were due to the presence of appropriate miRNAs as they exchanged with Strand 2 in the sample well containing their respective complimentary strands, and that no cross talking of magnetic signal is exhibited between let-7a and let-7c, thus the EXIRM method herein described has single-base specificity. In some embodiments, this capability is required for miRNA profiling because miRNAs in the same family often differ by only a few nucleotides; conventional techniques are often unable to obtain single base specificity especially in light of the short sequences often associated with miRNA's.

Materials and Methods.

In some embodiments, the biotinylated or thiol-derivitized first nucleotide strands were immobilized on the bottom surface of sample wells wherein the surface is streptavidin- or gold-coated. After hybridization with their corresponding biotinylated strand 2, with at least one mismatching base, the samples are incubated in on embodiment with streptavidin-conjugated magnetic particles (Invitrogen M280) at room temperature in tris-buffered saline (TBS) solution with 1% (w/v) bovine serum albumin (BSA) and 0.05% detergent Tween 20, the magnetic particles were then magnetized by a permanent magnet. The M280 particles are uniform, superparamagnetic beads of 2.8 mm in diameter with a streptavidin monolayer covalently bound to the surface. They are supplied as a suspension.

In some embodiments, to initiate the exchange reaction, the target DNA or miRNA with an entirely complementary sequence (to the capture probe) to strand, was then added and incubated in TE buffer (10 mM tris, 1 mM EDTA, 1 M NaCl, pH 8.0) at 37° C. The samples' magnetic signal was measured by an atomic magnetometer after applying a weak centrifugal force to eliminate physisorption of the magnetic particles. For the DNA exchange reaction, reaction time was varied between 20-220 min. For miRNA targets (let-7a and let-7c), two capture probes (1a and 1b) were located in two sample wells were placed on a sample holder, one with the double helix of Strand 1a and Strand 2, and the other with Strand 1b and Strand 2. The center-to-center distance between the sample wells was 14 mm. The reaction time was 6 hrs for miRNAs exchange.

In some embodiments, using miniature atomic magnetometers (23), EXIRM is capable of sensitive and precise miRNA profiling, and in some further embodiments will be used in cancer diagnostics.

While certain embodiments of the invention described herein specifically focus on a novel method to detect DNA and miRNA sequences of interest based on their specific binding pairs and specificity, one of ordinary skills in the art, with the benefit of this disclosure, will recognize the extension of the approach to other systems.

Other and further embodiments, versions and examples of the invention may be devised without departing from the basic scope thereof and the scope thereof is determined by

REFERENCES

1. Bartel, D. P. MicroRNAs: genomics, biogenesis, mechanism, and function. *Cell* 116, 182-297 (2004).
2. Alvarez-Garcia, I. & Miska, E. A. MicroRNA functions in animal development and human disease. *Development* 132, 4653-4662 (2005).
3. Lee, Y. S. & Dutta, A. MicroRNAs in cancer. *Annu. Rev. Pathol.* 4, 199-227 (2009).
4. Lagos-Quintana, M., Rauhut, R., Lendeckel, W. & Tuschl, T. Identification of novel genes coding for small expressed RNAs. *Science* 294, 853-858 (2001).
5. Benes, V. & Castoldi, M. Expression profiling of microRNA using real-time quantitative PCR, how to use it and what is available. *Methods* 50, 244-249 (2010).
6. Obernosterer, G., Martinez, J. & Alenius, M. Locked nucleic acid-based in situ detection of microRNAs in mouse tissue sections. *Nat. Protoc.* 2, 1508-1514 (2007).
7. Sudo, H., Mizoguchi, A., Kawauchi, J., Akiyama, H. & Takizawa, S. Use of non-amplified RNA samples for microarray analysis of gene expression. *Plos One* 7, 1-6 (2012).
8. Cissell, K. A., Rahimi, Y., Shrestha, S., Hunt, E. A. & Deo, S. K. Bioluminescence-based detection of MicroRNA, miR21 in breast cancer cells. *Anal. Chem.* 80, 2319-2325 (2008).
9. Fang, S. P., Lee, H. J., Wark, A. W. & Corn, R. M. Attomole microarray detection of MicroRNAs by nanoparticle-amplified SPR imaging measurements of surface polyadenylation reaction. *J. Am. Chem. Soc.* 128, 14044-14046 (2006).
10. Driskell, J. D., Seto, A. G., Jones, L. P., Jokela, S., Dluhy, R. A., Zhao, Y.-P. & Tripp, R. A. Rapid microRNA (miRNA) detection and classification via surface-enhanced Raman spectroscopy (SERS). *Biosens. Bioelectron.* 24, 917-922 (2008).
11. Yang, H., Hui, A., Pampalakis, G., Soleymani, L., Liu, F. F., Sargent, E. H. & Kelley, S. O. Direct, electronic MicroRNA detection for the rapid determination of differential expression profiles. *Angew. Chem. Int. Ed.* 48, 8461-8464 (2009).
12. Jiang, L., Duan, D. M., Shen, Y. & Li, J. Direct microRNA detection with universal tagged probe and time-resolved fluorescence technology. *Biosens. Bioelectron.* 34, 291-295 (2012).
13. Qavi, A. J., Kindt, J. T., Gleeson, M. A. & Bailey, R. C. Anti-DNA: RNA antibodies and silicon photonic microring resonators: increased sensitivity for multiplexed microRNA detection. *Anal. Chem.* 83, 5949-5956 (2011).
14. Reid, G., Kirschner, M. B. & van Zandwijk, N. Circulating microRNAs: association with disease and potential use as biomarkers. *Crit. Rev. Oncol. Hematol.* 80, 193-208 (2011).
15. Yao, L., Wang, Y. & Xu, S.-J. Ultrasensitive microRNA sequencing using exchange-induced remnant magnetization. *Chem. Commun.* 49, 5183-5185 (2013).
16. Savory, N., Abe, K., Sode, K. & Ikebukuro, K. Selection of DNA aptamer against prostate specific antigen using a genetic algorithm and application to sensing. *Biosens. Bioelectron.* 26, 1386-1391 (2010).
17. Yao, L. & Xu, S. Long-range, high-resolution magnetic imaging of nanoparticles. *Angew. Chem. Int. Ed.* 48, 5679-5682 (2009).
18. de Planell-Saguer, M. & Rodicio, M. C. Analytical aspects of microRNA in diagnostics: a review. *Anal. Chim. Acta* 699, 134-152 (2011).
19. Garcia, N. C. L., Yu, D., Yao, L. & Xu, S.-J. Optical atomic magnetometer at body temperature for magnetic particle imaging and nuclear magnetic resonance. *Opt. Lett.* 5, 661-663 (2010).
20. Yu, D. S., Ruangchaithaweesuk, S., Yao, L. & Xu, S.-J.* Detecting molecules and cells labeled with magnetic particles using an atomic magnetometer. *J. Nanoparticle Res.* 14, 1135 (2012).
21. Boeri, M., Pastorino, U. & Sozzi, G. Role of microRNA in lung cancer: MicroRNA signatures in cancer prognosis. *Cancer J.* 18, 268-274 (2012).
22. Schetter, A. J., Okayama, H. & Harris, C. C. The role of microRNAs in colorectal cancer. *Cancer J.* 18, 244-252 (2012).
23. Shah, V., Knappe, S., Schwindt, P. D. D. & Kitching, J. Subpicotesla atomic magnetometry with a microfabricated vapor cell. *Nat. Photon.* 1, 649-652 (2007).

What is claimed is:

1. A method of detecting nucleotide sequences, comprising
   a) immobilizing a first nucleotide single strand on a surface;
   b) adding a second nucleotide single strand to the first nucleotide single strand to form a hybridized double strand, wherein said second strand comprises:
      a first magnetic particle; and
      a nucleotide sequence that comprises at least one base that does not form a complementary base pair with said first nucleotide single strand;
   c) measuring a first magnetic signal value for said hybridized double strand;
   d) incubating a third nucleotide strand with said hybridized double strand; wherein said third strand is complementary to said first strand, and wherein said incubating forms an exchange product;
   e) measuring a second magnetic signal value for the exchange product of step d after applying a weak mechanical force and randomizing the magnetic dipoles of nonspecifically bound magnetic particles, wherein said measuring occurs in the absence of removing said nonspecifically bound magnetic particles from said surface; and
   f) quantifying the amount of said third nucleotide strand from the difference in magnetic signal values measured in step c and step e, wherein the difference in the magnetic signal values comprises a decrease in magnetic signal values due to the randomizing of the magnetic dipoles of the nonspecifically bound magnetic particles.

2. The method of claim 1, wherein said first nucleotide single strand is derivatized.

3. The method of claim 1, wherein said first nucleotide strand is immobilized to said surface through a S—Au covalent bond or by a streptavidin-biotin non-covalent bond.

4. The method of claim 1, wherein said first magnetic particle is about 1 nm to about 10 µm in size.

5. The method of claim 1, wherein said first and said second magnetic signal comprise magnetic moment measurements.

6. The method of claim 1, wherein said weak mechanical force is supplied by a shaker, centrifuge, or sonicator.

7. The method of claim 1, wherein said hybridized double strand is in a liquid environment, a cell lysate, blood plasma, or urine.

8. An exchange-induced remnant magnetization method to detect cancer biomarkers, the method comprising:
   (a) immobilizing a first sequence on a surface; wherein said first sequence comprises N bases;
   (b) adding a second sequence to said first sequence, wherein said second sequence comprises less than N complementary bases and a magnetic particle; and wherein said second sequence hybridizes to said first sequence forming a hybridized double strand;
   (c) measuring a first magnetic signal value for said hybridized double strand;
   (d) incubating said hybridized double strand with a cancer biomarker nucleic acid; wherein said cancer biomarker nucleic acid exchanges with said second strand to form an exchange product; wherein said exchange product is thermodynamically more stable than said hybridized double strand;
   (e) measuring a second magnetic signal value for the exchange product of step (d) after applying a weak mechanical force and randomizing the magnetic dipoles of nonspecifically bound magnetic particle, wherein said measuring occurs in the absence of removing said nonspecifically bound magnetic particles from said surface; and
   f) quantifying the amount of said cancer biomarker nucleic acid from the difference in magnetic signal values measured in step (c) and step (e) wherein the difference in the magnetic signal values comprises a decrease in magnetic signal values due to the randomizing of the magnetic dipoles of the nonspecifically bound magnetic particles.

* * * * *